(12) United States Patent
Chaudhary

(10) Patent No.: US 8,734,852 B2
(45) Date of Patent: May 27, 2014

(54) PARENTERAL CONTROLLED RELEASE FORMULATIONS OF NSAID'S

(76) Inventor: Manu Chaudhary, Haryana (IN)

( * ) Notice: Subject to any disclaimer, the term of this patent is extended or adjusted under 35 U.S.C. 154(b) by 0 days.

(21) Appl. No.: 13/344,538

(22) Filed: Jan. 5, 2012

(65) Prior Publication Data

US 2013/0136798 A1  May 30, 2013

(30) Foreign Application Priority Data

Nov. 30, 2011 (IN) .......................... 3449/DEL/2011

(51) Int. Cl.
*A61K 31/216* (2006.01)
(52) U.S. Cl.
USPC .......................................................... 424/497
(58) Field of Classification Search
CPC .................................................... A61K 9/0019
USPC .......................................................... 424/497
See application file for complete search history.

(56) References Cited

U.S. PATENT DOCUMENTS 7,825,150 B2 * 11/2010 Oravecz ........................ 514/400
2010/0291102 A1 * 11/2010 Dalgleish et al. .......... 424/158.1

FOREIGN PATENT DOCUMENTS

WO  WO 2010/008135  *  1/2010  ............... A61K 9/48

OTHER PUBLICATIONS

Gupta et al (Studies of in vitro Evaluation and Formulation of Aceclofenac Loaded PLGA Microspheres. International Journal of Pharmacology 6(5):726-731, 2010.*

* cited by examiner

*Primary Examiner* — Jake Vu
(74) *Attorney, Agent, or Firm* — Knobbe, Martens, Olson & Bear, LLP

(57) ABSTRACT

A controlled release parenteral formulation for treatment of pain and inflammation is provided. The formulation includes an effective amount of: one or more active drug moiety. The drug moiety is selected from a group comprising aceclofenac or diclofenac or a combination thereof; One or more solvent moiety selected from a group comprising one or more of ethyl acetate, triacetin, di methyl iso sorbide, DMA, DMSO, PEG, PVP, PVA, Span 80, DCM, Benzyl alcohol, acetone or a combination thereof. The formulation, upon administration, has a release profile including an immediate burst release and the burst release is followed by a slow release of at least 18 to 24 hrs. The immediate burst release and the slow release of the drug moiety remains within the therapeutic window of the drug moiety.

10 Claims, 8 Drawing Sheets

| Pain score chart in rat model | | | | | | | | | |
|---|---|---|---|---|---|---|---|---|---|
| Groups | Before induction | At the day of induction | Day 1 after treatment | Day 2 after treatment | Day 3 after treatment | Day 4 after treatment | Day 5 after treatment | Day 6 after treatment | Day 7 after treatment |
| Disease control | 0 | 6 | 6.5 | 5 | 6 | 5 | 4 | 3 | 1.5 |
| Aceclofenac (Aceclo) (OD) | 0 | 6.5 | 4.5 | 4 | 2.5 | 1.5 | 0 | 0 | 0 |
| Diclofenac (OD) | 0 | 6.5 | 5.5 | 4.5 | 3.5 | 2.5 | 1 | 0 | 0 |
| Diclofenac (BD) | 0 | 6 | 5.5 | 5 | 4.5 | 3 | 1 | 0.5 | 0 |
| Paracetamol (TD) | 0 | 6.5 | 6 | 5.5 | 5 | 3.5 | 1.5 | 1 | 0 |
| Ibuprofen (TD) | 0 | 6 | 5.5 | 4.5 | 4 | 3 | 1.5 | 0.5 | 0 |

FIG. 1

| Comparison of TNF alpha, ESR and CRP level parametrs as inflammtory reponse in pain &inflammation induced and treated groups after 7 days of treatment. | | | | | | |
|---|---|---|---|---|---|---|
| Aceclofenac group was compared to other antiinflammatory drugs for statistical significant (b, c, ) where b is ** ( p<0.01) where c is ***( p<0.001) | | | | | | |
| Groups | Disease control | Aceclofenac (OD) | Diclofenac (OD) | Diclofenac (BD) | Parcetamol (TD) | Ibuprofen (TD) |
| TNF alpha (IU/ml) | 1160 ± 49.5 | 773 ±11.31$^c$ | 833±43.28 | 853±38.18 | 918.5±9.19 | 879±7.78 |
| ESR level mm /hr | 9.8± 1.25 | 3.1± 0.98 $^c$ | 4.35±1.75 | 5.25±0.71 | 6.5±0.84 | 7.0± 1.01 |
| CRP level (mg/dL) | 8.25±0.45 | 2.56± 0.36$^c$ | 3.15± 0.98 | 3.15±0.48 | 5.10± 0.69 | 6.7± 0.56 |

FIG. 2

| Pharmacokinetic data comparison of immediate release marketed formulation (Hifenac injection) and aceclofenac formulations Aceclofenac OD and Aceclofenac 3D ||||
|---|---|---|---|
| Parameter | Control (Market Sample) Hifenac Injection | Aceclofenac 3D Aceclofenac SR suspended formulation | Aceclofenac OD Aceclofenac controlled release |
| Total AUC (ng.h/ml) | 6874.4 | 31283.08 | 17531.9 |
| Kel (h-1) | 0.246 | - | --- |
| T 1/2 | 2.816 | - | --- |
| $C_{max}$ (ng/ml) | 3477 | 1108 | 1876 |

| Dose Reduction and Treatment time Reduction observed in Phase III multi centric comparative clinical trials on 300 patients. | | | | | |
|---|---|---|---|---|---|
| Drug | Dosage Regimen | Treatment Duration | Cure Rate | Reduction in Treatment Time | Reduction in Dosing Interval |
| (Aceclofenac) Aceclofenac OD | Once Daily | 3 Days | 100% | 22% | 3*1= 3 injections |
| Diclofenac BD | Twice Daily | 3 days | 78% | ----- | 3*2= 6 injections |
| Infereneces | Dose is reduced to 50% in case of Aceclofenac OD with approx 22% reduction in treatment time. | | | | |

FIG. 7

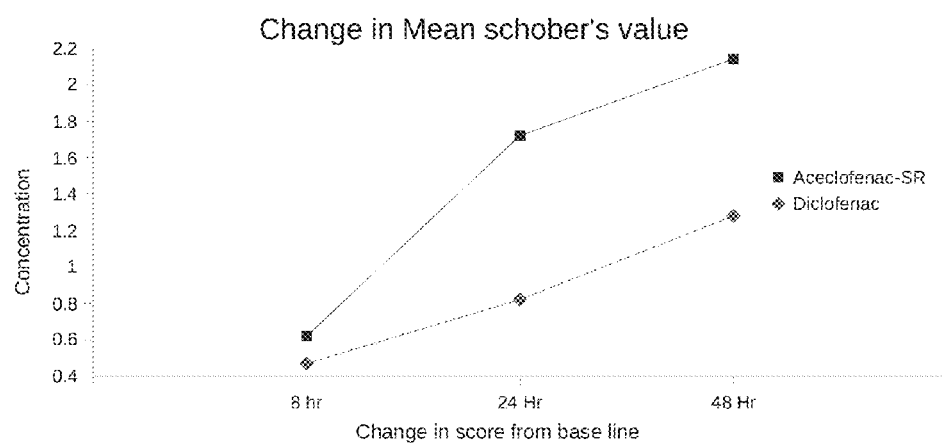

FIG. 8

| Stability Study Data of 150mg/3ml Aceclofenac OD Injection |
|---|
| Batch No. : 1EE1602 |
| Date of Mfg. : May- 2010 |
| Date of Exp. : April- 2012 |
| Storage Conditions : 25°C±2°C ,60%±5%RH |
| Packing : 3 ml ampoule |

| Period (Month) | Description | Extractable volume | Identification | Bacterial Endotoxins | Sterility | Particulate matter | | Assay Each ml contains: 50 mg Aceclofenac | Related Substances by HPLC | | |
|---|---|---|---|---|---|---|---|---|---|---|---|
| Specifications | Clear colorless to pale yellow solution. | (NLT 3.0ml) | (By HPLC) | NMT 1.17 EU/mg of Aceclofenac | (Should be sterile) | ≥10 microns NMT 6000 particles / container | ≥ 25 microns NMT 600 particles / container | (45 to 55 mg label claim) | Impurity A (Diclofenac) (NMT 2.0%) | Any unknown maximum impurity (NMT 0.5%) | Total impurities (NMT 3.0%) |
| Initial | Pale yellow solution. | 3.1ml | Complies | Complies | Sterile | 271 | 20.8 | 50.49 | 0.11 | 0.04 | 0.30 |
| 3 | Pale yellow solution. | 3.1ml | Complies | ----- | ----- | ----- | ----- | 49.75 | 0.14 | 0.06 | 0.38 |
| 6 | Pale yellow solution. | 3.2ml | Complies | ----- | ----- | ----- | ----- | 49.12 | 0.15 | 0.09 | 0.4 |
| 12 | Pale yellow solution. | 3.1ml | Complies | ----- | ----- | ----- | ----- | 48.98 | 0.18 | 0.13 | 0.48 |
| 18 | Pale yellow solution. | 3.2ml | Complies | ----- | ----- | ----- | ----- | 48.64 | 0.24 | 0.15 | 0.52 |

REMARKS: 1. All procedure carried out as per STP and Product is table for a shelf life of 18 months and more. Stability continued. (Test for BET, Sterility and Particulate matter is to be conducted in the beginning and at the end of study only).

FIG. 11

Stability Study Data of 300mg/2ml Aceclofenac SR Injection
Batch No. : 1EE1601
Date of Mfg. : May- 2010
Date of Exp. : April- 2012
Storage Conditions : 25°C±2°C ,60%±5%RH
Packing : 2 ml ampoule

| Period (Month) | Description | Extractable volume | Identification | Bacterial Endotoxins | Sterility | Particulate matter | | Assay Each ml contains: 150 mg Aceclofenac | Related Substances by HPLC | | |
|---|---|---|---|---|---|---|---|---|---|---|---|
| Specifications | Clear colorless to pale yellow solution. | (NLT 2.0ml) | (By HPLC) | NMT 1.17 EU/mg of Aceclofenac | (Should be sterile) | ≥10 microns NMT 6000 particles / container | ≥ 25 microns NMT 600 particles / container | (135 to 165 mg label claim) | Impurity A (Diclofenac) (NMT 2.0%) | Any unknown maximum impurity (NMT 0.5%) | Total impurities (NMT 3.0%) |
| Initial | Pale yellow solution. | 2.2ml | Complies | Complies | Sterile | 271 | 20.8 | 150.9mg | 0.24 | 0.07 | 0.45 |
| 3 | Pale yellow solution. | 2.1ml | Complies | ------ | ------ | ------ | ------ | 150.1mg | 0.37 | 0.08 | 0.57 |
| 6 | Pale yellow solution. | 2.2ml | Complies | ------ | ------ | ------ | ------ | 149.7mg | 0.49 | 0.11 | 0.68 |
| 12 | Pale yellow solution. | 2.1ml | Complies | ------ | ------ | ------ | ------ | 147.5 mg | 0.71 | 0.18 | 0.91 |
| 18 | Pale yellow solution. | 2.2ml | Complies | ------ | ------ | ------ | ------ | 140.1 mg | 0.99 | 0.21 | 1.1 |

REMARKS: 1. All procedure carried out as per STP and Product is table for a shelf life of 18 months and more. Stability continued. (Test for BET, Sterility and Particulate matter is to be conducted in the beginning and at the end of study only).

FIG. 12

| Stability Study Data of 150mg/ml Aceclofenac SR Injection |
|---|
| Batch No. : 1EE1603 |
| Date of Mfg. : May- 2010 |
| Date of Exp. : April- 2012 |
| Storage Conditions : 25°C±2"C ,60%±5%RH |
| Packing : 1 ml ampoule |

| Period (Month) | Description | Extractable volume | Identification | Bacterial Endotoxin | Sterility | Particulate matter | | Assay Each ml contains: 150 mg Aceclofenac | Related Substances by HPLC | | |
|---|---|---|---|---|---|---|---|---|---|---|---|
| Specifications | Clear colorless to pale yellow solution. | (NLT 1.0ml) | (By HPLC) | NMT 1.17 EU/mg of Aceclofenac | (Should be sterile) | ≥10 microns NMT 6000 particles / container | ≥ 25 microns NMT 600 particles / container | (67.5 to 82.5 mg label claim) | Impurity A (Diclofenac) (NMT 2.0%) | Any unknown maximum impurity (NMT 0.5%) | Total impurities (NMT 3.0%) |
| Initial | Pale yellow solution. | 1.1ml | Complies | Complies | Sterile | 271 | 20.8 | 74.9mg | 0.14 | 0.05 | 0.34 |
| 3 | Pale yellow solution. | 1.1ml | Complies | ------ | ------ | ------ | ------ | 75.1mg | 0.17 | 0.06 | 0.45 |
| 6 | Pale yellow solution. | 1.0ml | Complies | ------ | ------ | ------ | ------ | 73.2mg | 0.19 | 0.1 | 0.48 |
| 12 | Pale yellow solution. | 1.1ml | Complies | ------ | ------ | ------ | ------ | 72.9 mg | 0.21 | 0.15 | 0.55 |
| 18 | Pale yellow solution. | 1.0 ml | Complies | ------ | ------ | ------ | ------ | 71.6 mg | 0.29 | 0.18 | 0.59 |

REMARKS: 1. All procedure carried out as per STP and Product is table for a shelf life of 18 months and more. Stability continued. (Test for BET, Sterility and Particulate matter is to be conducted in the beginning and at the end of study only).

FIG. 13

PARENTERAL CONTROLLED RELEASE FORMULATIONS OF NSAID'S

CROSS-REFERENCE TO RELATED APPLICATION

This application claims the benefit under 35 U.S.C. §119 (a)-(d) of Indian Application No. 3449/DEL/2011, filed Nov. 30, 2011, the disclosure of which is hereby expressly incorporated by reference in its entirety and is hereby expressly made a portion of this application.

FIELD OF THE INVENTION

The field of invention pertains to pharmaceutical formulations. More specifically, it pertains to a novel controlled release drug delivery system for parenteral application of NSAID (non-steroidal anti-inflammatory drug) including aceclofenac/diclofenac.

BACKGROUND OF THE INVENTION

Non-steroidal anti-inflammatory drugs (NSAIDs) are considered to be the first-line drugs in the symptomatic treatment of rheumatoid arthritis, osteoarthritis and ankylosing spondylitis. Aceclofenac is one of the emerging NSAID molecules for arthritis treatment. It is a newer derivative of diclofenac and has less gastrointestinal complications.

Primary mechanism responsible for its anti-inflammatory, antipyretic, and analgesic action is inhibition of prostaglandin synthesis by inhibition of cyclooxygenase (COX). Inhibition of COX also decreases prostaglandins in the epithelium of the stomach, making it more sensitive to corrosion by gastric acid. This is also the main side-effect of diclofenac. Diclofenac has a low to moderate preference to block the COX2-isoenzyme (approximately 10-fold) and is said to have, therefore, a somewhat lower incidence of gastrointestinal complaints than noted with indomethacin and aspirin. Aceclofenac has higher anti-inflammatory action than conventional NSAIDs and this is a cytokine inhibitor. Aceclofenac works by blocking the action of a substance in the body called cyclo-oxygenase. Aceclofenac is essentially a phenyl acetic acid derivative and inhibits interleukin1b-induced prostaglandin E2 production but has poor COX-I inhibitor effect in oral form. Cyclo-oxygenase is involved in the production of various chemicals in the body, some of which are known as prostaglandins. Prostaglandins are produced in response to injury or certain diseases and would otherwise go on to cause pain, swelling and inflammation. In this respect, Arthritic conditions are one such example.

As long-term use of diclofenac and similar NSAIDs predisposes for peptic ulcer, many patients are at risk for this complication.

Presently, both Aceclofenac and Diclofenac are available commercially in the form of immediate release or sustained release tablets, capsules, gels, but injection formulations are available as only as immediate release as described by the Inventor's Indian Patent No. 236996.

Sustained release formulations of Aceclofenac and Diclofenac are commercially available in the form of film coated tablets, Capsules and gel.

Moreover, even though use of different means such as polymer, solvent or matrix has been proposed in the past for enhancing effectiveness of NSAIDs, there still remain challenges in terms of optimum drug loading in to solvent system, optimization size and stabilization drugs loaded system and to control and release of NSAIDS at a predefined and reproducible rate for prolonged period.

OBJECTS OF THE INVENTION

As mentioned herein above, there remains a strong societal need to formulate NSAIDs preparation that is effective to provide immediate relief to pain and inflammation and maintaining a desired therapeutic drug concentration level in the body for a substantially long period yet avoiding associated adverse drug reactions. The formulation must include applications in the form of controlled release and long acting parenteral formulation and alleviating patient suffering by reducing number of pricks, reducing dose and ADRs.

Accordingly, it is an object of the invention to disclose a novel parenteral controlled release formulation of aceclofenac/diclofenac that is therapeutically effective for much longer time than existing commercially available formulations.

Another object of the invention is to disclose a novel formulation of aceclofenac/diclofenac which is sustained release in injection form.

Yet another object of the invention is to disclose a novel formulation of aceclofenac/diclofenac which gives initial burst release to cater acute pain and then release is maintained for at least next 24 hrs or more.

Still another object of the invention is to disclose a formulation which maintains release in vivo with in therapeutic window of the drug used and hence is devoid of side effects caused by crossing the drug levels in super therapeutic levels.

Still another object of the invention is to disclose a novel formulation of aceclofenac/diclofenac which has better patient compliance owing to lower frequency of dosing and lesser number of pricks.

One more object of the invention is to disclose an improved formulation which has considerably reduced side effects owing to dose reduction and lesser administration than existing formulations.

SUMMARY OF THE INVENTION

In view of the foregoing, a controlled release parenteral formulation for treatment of pain and inflammation is provided. The formulation include an effective amount of: one or more active drug moiety and the drug moiety is selected from a group that include aceclofenac or diclofenac or a combination thereof; at least a solvent moiety and the solvent moiety is selected from a group that include one or more of ethyl acetate, triacetin, di methyl iso sorbide, N,N Dimethyl acetamide, Dimethyl sulphoxide, Poly ethele glycol, Poly vinyl pyrrolidone, Polyvenyl alcohol, polysorbate 80, Dichloromethane, Benzyl alcohol, acetone or a combination thereof. The formulation, upon administration, has a release profile include an immediate burst release. The burst release is followed by a sustained release of at least 18 to 24 hrs. The immediate burst release and the sustained release of the drug moiety remains within the therapeutic window of the drug moiety. The solvent and the drug moiety are present as a single unit injection.

The drug moiety may be present in a range of 1 mg to about 500 mg of the formulation.

The drug moiety may aceclofenac or a pharmaceutical acceptable salt thereof.

The solvent moiety may be selected from group include dimethyl iso sorbide in a range of about 0.05 ml to about 0.7 ml.

The solvent moiety may be selected from a group include triacetin in a range of about 0.3 ml to about 3.0 ml.

The drug moiety may be Acelofenac or a pharmaceutically acceptable salts thereof a Aceclofenac may be present in a arrange of about 50 mg/ml to about 200 mg/ml.

The solvent moiety may include dimethyl iso sorbide and triacetin and ratio of dimethyl iso sorbide:triacetin may be in a range of about 1:4.5 to about 1:5.5.

The controlled release parenteral formulation may be a liquid injection ready to use as the single unit injection and the pH of the formulation may be 5.0±1.0.

The controlled release parenteral formulation may further include a plurality of micro-sphere that include a polymer moiety to encapsulate the drug moiety.

The polymer moiety may include one or more polymer selected from the group include of PLGA.

PLGA may include about 1:3 molar ratio of glycolic acid:lactic acid.

The PLGA may have molecular weight of about 80 KDa to 150 KDa, preferably about 50 KDa to about 130 Kda.

The drug moiety along with the polymer moiety and solvent moiety may form a sustained release delivery system for at least 24 hrs or more, preferably 72 hrs and the formulation may be administered using a suitable dispensing medium.

The dispensing medium may include about 0.5% to about 1.5% of carboxymethyl cellulose (CMC), about 0.1% to 1.0% polysorbate 80, about 1.0 mM to about 10 mM sodium dihydrogen orthophosphate along with an effective amount of NaCl for rendering osmolarity of the dispensing medium of about 290 m mol/kg and an effective amount of NaOH to obtain a pH range of about 7.0±1.0, preferably 7.4.

The dispensing medium may include preferably about 1% CMC and preferably about 0.5% polysorbate 80.

Size of the micro-sphere may be about 20 to 120 micron, preferably about 40 to about 70 micron, more preferably about 30 to 60 micron.

In another aspect a method of effecting sustained release of a controlled release parenteral formulation for treatment of pain and inflammation along with reducing post surgical adhesions associated with medical conditions in an animal in need is provided.

The method may include the steps of administering not more than one injection to a subject in need an effective amount of the formulation in a three days period.

In yet another aspect use of a controlled release parenteral formulation for preparation of an medicament is provided.

The medicament may be used to relieve pain and inflammation in medical conditions include surgical pain, spasmodic pain, muscular pain, cramps, nociceptive pain, idopathic pain, neuropathic pain, psychogenic pain, phantom pain, accidental and sports injury pain, surgical pain and post surgical adhesion pain, rheumatoid arthritis, spondyloarthropathies particularly ankylating spondalosis, osteoarthritis, systemic lupus erythematosus and juvenile arthritis; asthma, bronchitis, preterm labor, tendonitis, bursitis, allergic neuritis, cytomegalovirus infection, apoptosis including HIV-induced apoptosis, lumbago, pain related to auto immune disorders.

BRIEF DESCRIPTION OF THE DRAWINGS

The embodiments herein will be better understood in terms of their characteristics and effectiveness from the following detailed description with reference to the figures depicting various test results:

FIG. 1 illustrates a Pain Score Chart illustrating comparative efficacy study of controlled release Once Daily Aceclofenac and Diclofenac with other commercial products with thrice daily administration in inflammation & pain induced rat model.

FIG. 2 illustrates a comparison of TNF alpha, ESR and CRP level parameters as inflammatory response in pain & inflammation induced and treated groups after 7 days of treatment.

FIG. 7 illustrate a Dose Reduction and Treatment time Reduction observed in Phase III multi centric comparative clinical trials on 300 patients.

FIG. 8 illustrates a Change in Pain score in Phase III Clinical trial.

FIG. 11 illustrates a Stability Study Data of 150 mg/3 ml Aceclofenac OD Injection.

FIG. 12 illustrates a Stability Study Data of 300 mg/2 ml Aceclofenac SR Injection.

FIG. 13 illustrates a Stability Study Data of 150 mg/ml Aceclofenac SR Injection.

DETAILED DESCRIPTION OF THE INVENTION

Figures 3, 4:
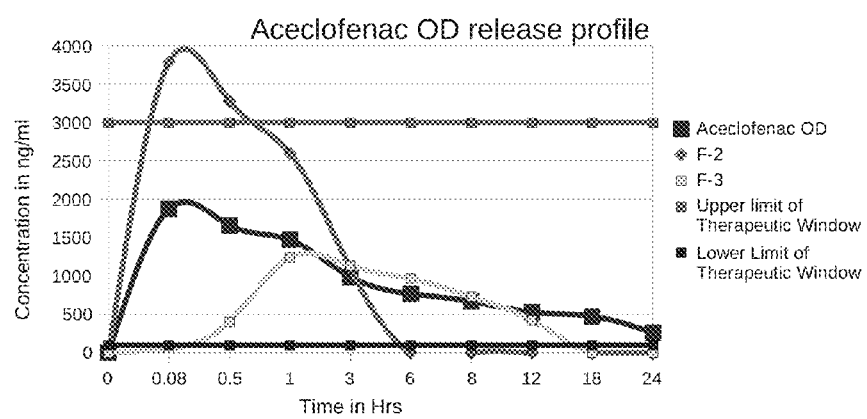
FIG. 3 illustrates a Pharmacokinetic data comparison of marketed formulation (Hifenac injection) and proposed aceclofenac particulate formulations.
FIG. 4: illustrates a comparative In Vivo Release study of Aceclofenac OD (Example 1) and other trial formulations with varied concentration ranges of solvents.

The embodiments herein and the various features and advantageous details thereof are explained more fully with reference to the non-limiting embodiments that are illustrated in the accompanying figures & tables and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In one embodiment of the invention, a controlled release parenteral pharmaceutical formulation of NSAID is provided. The NSAID is selected from the group comprising one or more drug moiety Aceclofenac/diclofenac or a combination thereof. The controlled release parenteral pharmaceutical formulation has a release profile that includes an immediate burst release of the drug moiety partially following a sustained/slow release of the remaining drug at least for a period of 24 hrs or more.

In another embodiment, the drug from the controlled release pharmaceutical formulation is released and remains within corresponding therapeutic window of the drug for the period mentioned herein above.

According to yet another embodiment formulation is dissolved in one or more solvents. The solvents may be a polymeric one or non polymeric one.

According to yet another embodiment formulation is dissolved in preferably two solvents, one catering to immediate burst release of drug within therapeutic window and other entrapping the drug for sustained release within therapeutic window to be released over a period of time for parenteral use.

According to a preferred embodiment the present invention provides a controlled release parenteral formulation for the treatment of pain and inflammation in single unit form. The controlled release parenteral formulation includes one or more active drug moiety selected from a group comprising aceclofenac or diclofenac or a combination thereof. One or more solvent moiety selected from a group comprising ethyl acetate, triacetin, di methyl iso sorbide, N,N Dimethyl acetamide, Dimethyl sulphoxide, Poly ethele glycol (PEG), Poly vinyl pyrrolidone, Polyvenyl alcohol, polysorbate 80, Dichloromethane, Benzyl alcohol, acetone or a combination thereof. The controlled release parenteral formulation, upon administration, has a release profile that includes an immediate burst release followed by a sustained/slow release of at least 18 to 24 hrs or more. The release remains within the therapeutic window of the said drug moiety for the entire period mentioned herein above.

In one embodiment, the controlled release parenteral formulation includes the drug moiety in an amount ranging about 1 mg to about 500 mg.

In a preferred embodiment, the controlled release parenteral formulation includes the drug moiety in an amount ranging about 50 mg/ml to about 200 mg/ml.

In a preferred embodiment of formulation the drug moiety aceclofenac is present as non water soluble salt and diclofenac as water soluble salt preferably sodium, potassium or pharmaceutically acceptable salts thereof.

In the most preferred embodiment, the drug moiety is aceclofenac or a pharmaceutical acceptable salt thereof.

In yet another embodiment, the controlled release parenteral formulation includes the drug moiety in an amount of 50 mg/ml to about 200 mg/ml wherein the drug moiety is dissolved in one or more of the solvent moiety. The solvent moiety is preferably a combination of dimethyl iso sorbide and triacetin. Dimethyl iso sorbide and triacetin is present in ratio of about 1:4.5 to about 1:5.5.

In one of the preferred embodiment, the controlled release parenteral formulation includes aceclofenac or a pharmaceutical acceptable salt thereof in an amount of 50 mg/ml to about 200 mg/ml. Aceclofenac is dissolved in the solvent wherein dimethyl iso sorbide is present in a range of about 0.05 ml to about 0.7 ml and triacetin present in a range of about 0.3 ml to about 3.0 ml.

In one of the most preferred embodiment, the controlled release parenteral formulation wherein aceclofenac or a pharmaceutical acceptable salt thereof is present in an amount of about 50 mg/ml to about 200 mg/ml and wherein solvent moiety includes dimethyl iso sorbide and triacetin in a ratio of 1:4.5 to about 1:5.5. It was surprising to found that this ratio of the solvent mentioned herein along with the drug moiety is critical for obtaining a stable parenteral delivery system of the drugs wherein there is an immediate release of the drug followed by a sustained/slow release that remains within the therapeutic window for a substantially longer period. It was also observed that any variation in the concentrations of either solvent beyond the given ratio disturbs the release profile. This result is illustrated in FIG. 4 wherein formulation of Example 1 mentioned later is taken as reference.

According to yet another embodiment, the solvent moiety that includes dimethylisosorbide and triacetin in a ratio of about 1:4.5 to about 1:5.5 are found to be responsible for initial burst release of aceclofenac giving relief to acute pain by keeping the release of drug within therapeutic window and sustaining the release of drug after a few minutes for a period of about at least 18 to 24 hrs within therapeutic window only, thereby giving relief to patient without further dose/injection administration.

In another embodiment, the controlled release parenteral formulation is present in a ready to use injection wherein pH is about 4.0 to about 7.0, preferably about 5.0±1.0.

According to another preferred embodiment of the controlled release parenteral formulation, the said solvent moiety and said drug moiety are present as single unit injection and the controlled release parenteral formulation is stable for a shelf life of 2 years. The stability of the controlled release parenteral formulation is described in FIG. 11 through FIG. 13.

In one embodiment of the controlled release parenteral formulation, aceclofenac/diclofenac is expressed as free acid present in the range from about 1 mg/ml to 300 mg/ml, more preferably from 50 mg/ml to about 200 mg/ml.

In yet another embodiment of the invention, the controlled release parenteral formulation optionally includes: a plurality of micro-sphere that includes a polymer moiety to encapsulate the drug moiety. The polymer includes one or more polymer selected from the group comprising of PLGA. PLGA has molecular weight of about 80 to 150 KDa, preferably about 50 to 130 KDa in 1:3 molar ratio of glycolic acid:lactic acid to form a sustained release delivery system. In this respect the controlled release parenteral formulation has a release profile of at least 24 hrs. The controlled release parenteral formulation is administered using a suitable dispensing medium. The drug moiety is preferably aceclofenac or a pharmaceutically acceptable salt thereof and the drug moiety is entrapped in the polymer moiety with the help of ethyl acetate. This is mentioned herein that the ethyl acetate is used herein as a further solvent in addition to the solvent used herein before and as part of element of processing condition to obtain the micro-spheres. Ethyl acetate is evaporated subsequently during processing to obtain the micro-spheres. The size of micro-sphere is about 20 to about 120 micron, preferably about 40 to about 70 micron, more preferably about 30 to 60 micron. The optimization of the size of the micro-spheres are essential to effect a desired loading of the drug moiety into the micro-sphere resulting in sustained/slow release of drug moiety.

According to one of the embodiment, the controlled release parenteral formulation includes the drug encapsulated in polymer is further dispersed in a matrix in the form of polymeric microspheres.

In another embodiment of the invention, the micro-spheres are formed by a process of lyophilization.

In one embodiment, the suitable dispensing medium includes about 0.5 to about 1.5% carboxymethyl cellulose (CMC), preferably 1% CMC, about 0.1% to about 1.0% polysorbate 80, preferably 0.5% polysorbate 80 and about 1.0 mM to about 10 mM sodium dihydrogen orthophosphate, an effective amount of NaCl for rendering osmolarity of said dispensing medium of about 290 m mol/kg and an effective amount of NaOH to obtain a pH range of about 7.0±1.0, preferably 7.4.

In another embodiment, the controlled release parenteral formulation includes a high amount of the drug moiety consisting of Aceclofenac/Diclofenac that is/are entrapped and the controlled release parenteral formulation releases the drug at a controlled rate following injection through intramuscular route and keeps the drug in blood stream for several hours/days at desired therapeutic levels.

According to still another embodiment, particle size of the micro-sphere is in a range of about 20 µm to about 120 µm, more specifically about 30 µm to about 60 µm to obtain a injectability through 22 G needle.

In yet another embodiment of the invention, the drug moiety is present in an amount of 1 mg/ml to about 300 mg/ml of the formulation.

In another embodiment, the controlled release parenteral formulation is present in a lyophilized form and is dispensed in a suitable medium to form suspension prior to administration.

Yet another embodiment is that the said drug is encapsulated/entrapped in a matrix which is in the form of organic non polymeric solvent.

In a preferred embodiment, the pharmaceutical formulation of the present invention is administered through a parenteral route.

In a further embodiment, the controlled release parenteral formulation is used for preparation of a medicament for treating pain and inflammation conditions comprising surgical pain, spasmodic pain, muscular pain, cramps, nociceptive pain, idopathic pain, neuropathic pain, psychogenic pain, phantom pain, accidental and sports injury pain, surgical pain and post surgical adhesion pain, rheumatoid arthritis, spondyloarthropathies particularly ankylating spondalosis, osteoarthritis, systemic lupus erythematosus and juvenile arthritis; asthma, bronchitis, preterm labor, tendonitis, bursitis, allergic neuritis, cytomegalovirus infection, apoptosis including HIV-induced apoptosis, lumbago, pain related to auto immune disorders.

The pain and inflammation also relates to condition of rheumatoid arthritis, spondylo arthropathies particularly ankylating spondalosis, osteoarthritis, systemic lupus erythematosus and juvenile arthritis. Both drugs are useful in the treatment of pain and inflammation caused by asthma, bronchitis, menstrual cramps, preterm labor, tendonitis, bursitis, allergic neuritis, cytomegalovirus infection, apoptosis including HIV-induced apoptosis, lumbago, migraine headaches, periartheritis, thyroiditis, aplastic anemia, Hodgkin's disease, scleroderma, rheumatic fever, type 1 diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, ophthalmic disorders, including without limitation inflammatory disorders such as endophthalmitis, episcleritis, retinitis, iriditis, cyclitis, choroiditis, keratitis, conjunctivitis and blepharitis, inflammatory disorders of more than one art of the eye, e.g., retinochoroiditis, iridocyclitis, iridocyclochoroiditis (also known as uveitis), keratoconjunctivitis, blepharoconjunctivitis, etc.; other COX-2 mediated retinopathies; ocular photophobia; acute trauma of any tissue of the eye including postsurgical trauma, e.g., following cataract or corneal transplant surgery; postsurgical ocular inflammation; intraoperative miosis in terms of retinal, neovascularization including that following injury or infection; macular degeneration; cystoid macular edema; retrolental fibroplasia and neovascular glaucoma.

The controlled release parenteral formulation has reduced potential for gastrointestinal toxicity and gastrointestinal irritation, including upper gastrointestinal ulceration and bleeding, in comparison with compositions of conventional NSAIDs. There is a substantial reduction in the dose of administered drug when compared with available therapy. The reduction in the dose is attributable to the sustained/slow release profile. The sustained/slow release not only leads to economic advantage but also results in reduction of toxic side effects as there is no drug release in super therapeutic zone.

According to another embodiment, the controlled release parenteral formulation of Aceclofenac/Diclofenac is used to prepare a medicament to relieve pain and inflammation in arthritic conditions including but not limited to rheumatoid arthritis, spondyloarthropathies particularly ankylating spondalosis, osteoarthritis, systemic lupus erythematosus and juvenile arthritis. Both drugs are useful in the treatment of pain and inflammation caused by asthma, bronchitis, menstrual cramps, preterm labor, tendonitis, bursitis, allergic neuritis, cytomegalovirus infection, apoptosis including HIV-induced apoptosis, lumbago, skin related conditions such as psoriasis, eczema, acne, burns, dermatitis and ultraviolet radiation damage including sunburn, and postoperative inflammation including that following ophthalmic surgery such as cataract surgery or refractive surgery.

According to yet another embodiment of the invention the said formulation of Aceclofenac/Diclofenac is used in treating pain and inflammation in such diseases as migraine headaches, periartheritis, thyroiditis, aplastic anemia, Hodgkin's disease, scleroderma, rheumatic fever, type 1 diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

According to another preferred embodiment of the invention the said formulation of Aceclofenac has extended application because of its ability to reduce post surgical adhesion and also finds applications in the treatment of pain and inflammation caused by ophthalmic disorders, including without limitation inflammatory disorders such as endophthalmitis, episcleritis, retinitis, iriditis, cyclitis, choroiditis, keratitis, conjunctivitis and blepharitis, inflammatory disorders of more than one art of the eye, e.g., retinochoroiditis, iridocyclitis, iridocyclochoroiditis (also known as uveitis), keratoconjunctivitis, blepharoconjunctivitis, etc.; other COX-2 mediated retinopathies; ocular photophobia; acute trauma of any tissue of the eye including postsurgical trauma, e.g., following cataract or corneal transplant surgery; postsurgical ocular inflammation; intraoperative miosis; ocular, for example retinal, neovascularization including that following injury or infection; macular degeneration; cystoid macular edema; retrolental fibroplasia; neovascular glaucoma; and ocular pain.

According to another embodiment of the invention the said formulation of Aceclofenac/Diclofenac has reduced potential for gastrointestinal toxicity and gastrointestinal irritation, including upper gastrointestinal ulceration and bleeding, by comparison with compositions of conventional NSAIDs.

According to another embodiment of the invention the said formulation of Aceclofenac/Diclofenac is used in treatment of pain caused by pulmonary inflammation; certain central nervous system disorders and also that caused by allergic rhinitis, respiratory distress syndrome, endotoxin shock syndrome and liver disease; postoperative pain, dental pain, muscular pain, and pain resulting from cancer. Besides being a useful product for drug delivery in humans, compositions of the present invention and formulations made thereof are also useful for veterinary treatment of companion animals, exotic animals, farm animals, and the like, particularly mammals.

It is mentioned that the controlled release parenteral formulation as mentioned herein above has many advantages that it caters to both immediate release giving relief in acute pain within a few minutes and to sustained release afterwards, for short half-life drugs, sustained release means less frequent dosing and thus better compliance, reduce variations in plasma/blood levels for more consistent result. Plasma drug levels within a defined therapeutic range are maintained for a long period, improved patient compliance owing to reduction in the number of doses taken by a patient and reducing number of pricks, enhanced drug safety profiles owing to reduced side effects/adverse effects because drug never crosses therapeutic window safety levels, longer duration of treatment with single prick.

In a preferred embodiment of the invention, the controlled release parenteral formulation has a reduced dosing frequency by providing and sustaining the therapeutic effect for a 18 to 24 hrs or more. The dose reduction is achieved by the fact that a single injection of the controlled release parenteral formulation is maintaining its effect in therapeutic window for 24 hrs or more. The reduction in side effects is achieved due to the controlled release parenteral formulation never exceeds therapeutic window. Similarly a reduction in adverse drug reactions is achieved by the controlled release parenteral formulation due to the fact that the amount of drug administered is reduced from 30-50% from the conventional immediate release drug formulations. This is described and represented through res the FIG. 7.

Further, as described herein before, the correct selection of appropriate solvent that too in a precise amount and designing of processing parameters that can release the drug in controlled manner over a period of several hours/days was a strong challenge. Conventional sustained release formulations provide long term release of a particular drug concentration without variation and fail to provide immediate effect.

For the purpose of different embodiment describe herein before and after, a controlled release formulation is defined as a formulation the release of which is controlled and designed to give initial burst release to cater initial acute pain management and then the effect is sustained for a longer period. A controlled release formulation differs from conventional sustained release formulations in many ways including but not limited to achieving desired release profile with immediate release that too in therapeutic window. Conventional sustained release formulations usually start efficacy after several hrs or days and effect is maintained for very long period of time and designed to avoid dose missing by a patient when a drug is to be taken regularly without miss for a very long period of time, may be several months. Other sustained release products are depot in nature and deposited in any part of the body to release drug slowly over a period of time and fail to provide immediate burst release within a few minutes of administration.

The controlled release parenteral formulation of the current invention is designed in such a way so as to release aceclofenac/diclofenac partially immediately providing relief within a few minutes, preferably in less than 5 minutes of administration following a sustained/slow release resulted by the use of the solvent moiety in specific range/ratio wherein the release is within the therapeutic window of the aceclofeac/disclofenac over substantially long period of time which is at least 24 hrs or more. Alternatively the release may be up to several days.

Several technical barriers as overcome in different embodiments of the present invention include, High dosing, Polymer/Matrix/Solvent selection and drug encapsulation. Since, aceclofenac is a water insoluble drug and 150 mg to 300 mg daily dose is required to be trapped in a solvent/matrix for intramuscularly injection, this limits administrable volume of injection to <3 ml. Owing to these challenges, it was difficult to design a formulation for Aceclofenac, in a sustained release formulation. Though diclofenac is soluble in water but aqueous formulation can not retain the drug for more than 8 hr inside body and thus needs repeated administration leading to increased toxicity and gastric side effects. Further, in this respect, various polymers were screened and was observed that at high dose of drugs, there occurs a phase separation (i.e. Separation of the drug from the polymer/non polymeric solvent itself) and this renders a parenteral formulation of NSAIDs impossible for controlled release application. Furthermore, the critical factor for obtaining the controlled release parenteral formulation as mentioned herein before was the correct choice of the solvent/matrix in which drug is to be dissolved for sustained release. Some of the challenges encountered were effective drug loading with desired release rates, limiting clumping of drug particles that occurs due to interaction of drug molecule at their surface, optimizing the stability. Another challenge in polymeric solvent based formulation prepared by lyophilizing microspheres is re-dispersion of the drug particle upon reconstitution. These problems made it appear that it was not possible to make a sustained release formulation of said drug molecules.

In one embodiment, a novel approach was adopted for encapsulation and it was found that PLGA at 1:3 molar ratio of glycolic acid and lactic acid content in polymeric backbone with molecular weight range of 50 KDa to 150 KDa can hold a high dose of drug up to 40%. The same can also release the drug in sustain release manner which makes it suitable for designing a formulation upto 3 days. It was further found that molecular weight of PLGA in the range of 80 KDa to about 130 KDa was particularly well suited for Example 2 describe herein after.

In an representative illustration, Example 2 of current invention involved overcoming important barriers as following: Identification of a polymer suitable for high drug loading of drug molecules, correct ratio of the polymer moiety, molecular weight of the polymers, size and stabilization of particulate formulation, Drying and lyophilization of the particulate form to make a stabilized formulation for extended shelf life, Suspending solution to deliver the particulate formulation through injection intramuscularly.

According to one of the embodiment of the invention, a number of solvents are selected from a group of non-halogenated organic solvent, more specifically ethyl acetate, triacetin, di methyl iso sorbide, DMA, DMSO, PEG, PVP, PVA, Span 80, Trehlose, DCM, Benzyl alcohol, acetone, and the like. The solvent system showing good solubility preferably more than 150 mg/ml was selected for particle preparation.

Aceclofenac has a tendency to convert into its isomeric form diclofenac immediately upon dissolution in most of the solvents. Diclofenac has known huge side effects and hence the aceclofenac formulations formed conventionally are able to manage pain but fail to provide safety associated with aceclofenac molecule owing to its rapid conversion. Current formulation was designed in such a way that conversion of aceclofenac to diclofenac was restricted and diclofenac was considered as one of the impurity in aceclofenac parenteral preparations by choice of solvents and their ratio optimization. (FIG. 11 to FIG. 13)

According a preferred embodiment Ethyl acetate is the solvent of choice for preparation of sustained release formulation for more than 3 days using polymeric microspheres.

According to yet another embodiment DMI is the choice of solvent for immediate release and triacetin is the preferred choice for sustained release effect for 24 hrs of an representative illustration through Example 1 which is describe in more detailed hereinafter.

According to a preferred embodiment, in the illustrative Example 2, the size of the micro-particle ranges between 40 micron to 70 micron for sustained release of drug over several days. The micro-particles are stabilized in an emulsion form using surfactants known to a person skilled in art which is polyvinyl alcohol (PVA) in current invention. The Example 2 is a lyophilized formulation which is suspended in the dispensing medium that include about 1.0% carboxymethyl cellulose (CMC), about 0.5% SPAN-80, about 10 mM sodium dihydrogen orthophosphate, required quantity of NaCl to obtain an optimum osmolilaty (290 m mol/kg) and required amount of NaOH to optimize the pH at about 7.4. The dispensing medium was formulated that was able to hold about 1.0 g micro-sphere particles and also extended a sedimentation of particles up to 5 min that is found to be sufficient for injection of any product according to an embodiment herein.

The Example 1 is an illustration of Aceclofenac OD (Once Daily formulation) wherein a non polymer solvent is selected from a group of solvents which is preferably dimethyl isosorbide in a range of about 0.05 ml to about 0.7 ml, preferably about 0.5 ml is mixed with aceclofenac or a pharmaceutically salt thereof. Aceclofenac when mixed, is present in a range of about 1 mg to about 300 mg, preferably 50 mg to 200 mg with continuous stirring under inert gas atmosphere for about 15 to about 30 min. To this solution another non polymeric solvent which is a triglyceride and known as 1,2,3-triacetoxypropane or glycerine triacetate, in a range from 0.5 ml to about 3.0 ml, preferably about 1.0 ml to about 2.5 ml, is mixed at a slow stirring for about 0.5 to 4 hrs under inert gas atmosphere till a clear solution is formed under controlled processing conditions. The solution is sterilized using 0.2 micron or equivalent filter as per acceptable pharmaceutical norms and filled and sealed in air tight container. The ratio of DMI:Triacetin is 1:4.5 to 1:5.5.

Figure 5:
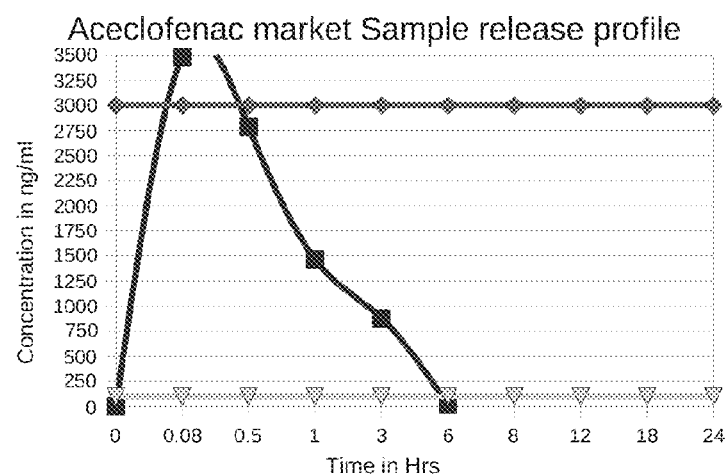
FIG. 5 illustrates an In Vivo Release study of (commercially available marketed formulation).
Figure 6:
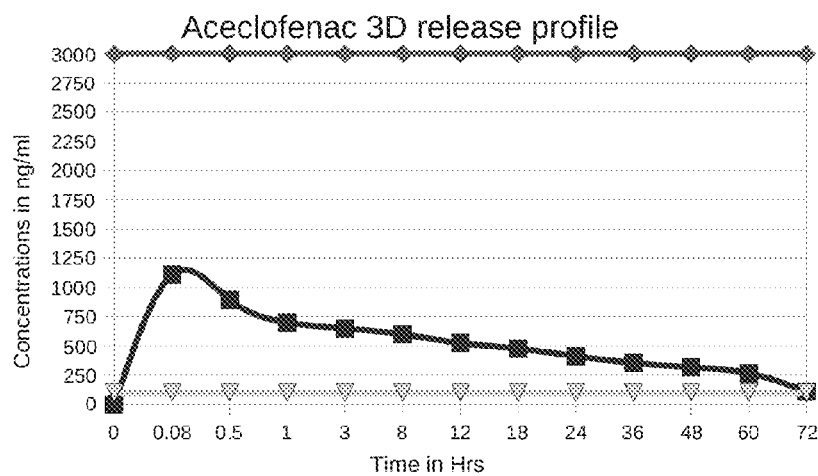
FIG. 6 illustrates an In Vivo Release study of Example 2 (Aceclofenac 3D—once in 3 day formulation).
Figure 9:
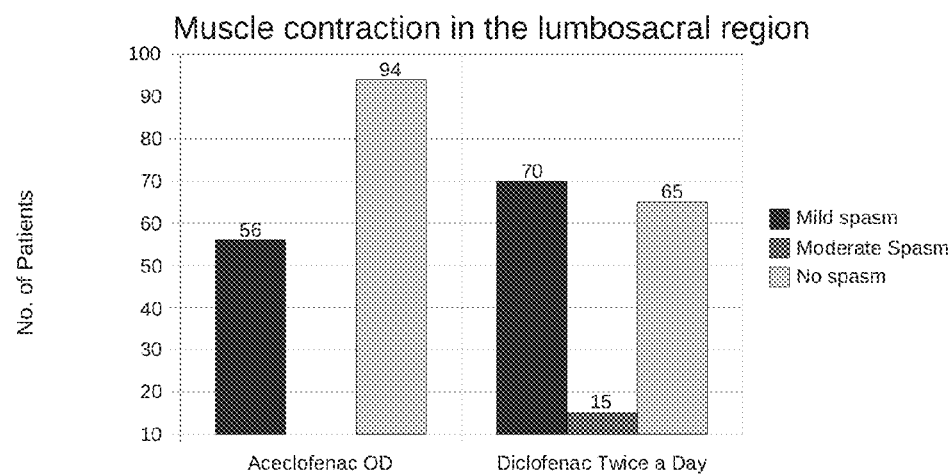
FIG. 9 illustrates a comparative efficacy of Aceclofenac OD compared with Diclofenac BD in Phase III clinical trial in 300 patients, expressed in terms of muscle contraction in lumbosacral region.

The Example 2 is an illustration of Aceclofenac 3D (once in 3 day formulation) wherein Polymer PLGA is at 1:3 molar ratio of glycolic acid and lactic acid content with average molecular weight (Mw) of 130 KDa, number average molecular (Mn) of 76 KDa and polydispersity of about 1.7, is first dissolved in about 5 ml to about 50 ml of ethyl acetate, preferably about 25 ml following addition of aceclofenac in an amount of about 0.5 g to about 2.0 g, preferably about 1.6 g. Ethyl acetate is allowed to evaporate for 12 h and solid micro-sphere are obtained. The micro-particles were filtered and washed thoroughly using distilled water. A suitable cryoprotectant is added which is known to a person skilled in art such as Trehalose (5% w/w), a disaccharide is added in the solution form containing the micro-particles and the resultant solution is lyophilized. Micro-sphere thus formed are sterilized using gamma radiation and are dispersed in sterile dispersion medium before administration. It was also observed that any deviation from the ratios and ranges of the solvent moiety, drug moiety and polymer as mentioned herein renders a failure to give desired results. Either the drug is released quickly, crossing therapeutic window barrier and reaches in super therapeutic zone and release is not maintained for 24 hrs and also the drug fail to provide initial burst release to cater acute pain. The same has been illustrated in FIG. 5.

In an illustration of the embodiment of the invention, Example 3 is represented wherein a Pharmacokinetic profile comparison of Aceclofenac OD (Aceclofenac once daily), Aceclofenac 3D (Aceclofenac once in 3 days) and Hifenac TID (Commercially available Aceclofenac immediate release formulation), based on In vivo release profile of all three drugs of comparison in human volunteers pK value is calculated and represented in FIG. 3.

In another illustration of the embodiment of the invention, Example 4 is represented wherein a Comparative efficacy study of controlled release Once Daily Aceclofenac and Diclofenac with other commercially available products with thrice daily administration in Inflammation & pain induced rat model is studied. A total of 30 healthy male rats were taken, all animals were anesthetized by ketamine injection. Then inflammatory pain was induced by 1 mg of Mono sodium iodo acetate (MIA), intra articular injection in left knee (Approx 50 microliter). Blood sample were also taken for biochemical parameters from all animals after 7 days of treatment. Pain score was measured on each day using a method. (Ref. MS; Laboratory Animal Resources, Colorado State University, Ft. Collins, Colo. 80523). Aceclofenac (Aceclofenac OD, Diclo OD) treated group shown a fast reduced pain score (FIG. 1) at all day interval then other treated groups. This study concluded that the Aceclofenac OD (example 1) has strongest analgesic & anti-inflammatory activity even at once daily dose and have immediate effect also, then comes diclofenac OD dose which has superior efficacy as compared to other market drugs which was given at twice & thrice daily doses. (i.e. Diclofenac (BD), Paracetamol (TD), Ibuprofen (TD), conventional forms. Results are expressed for Pain score in FIG. 1 and TNF alpha, ESR etc in FIG. 2 (All data mean±SD. P value was analyzed by Newman Kaul test for statistically significant).

Figure 10:
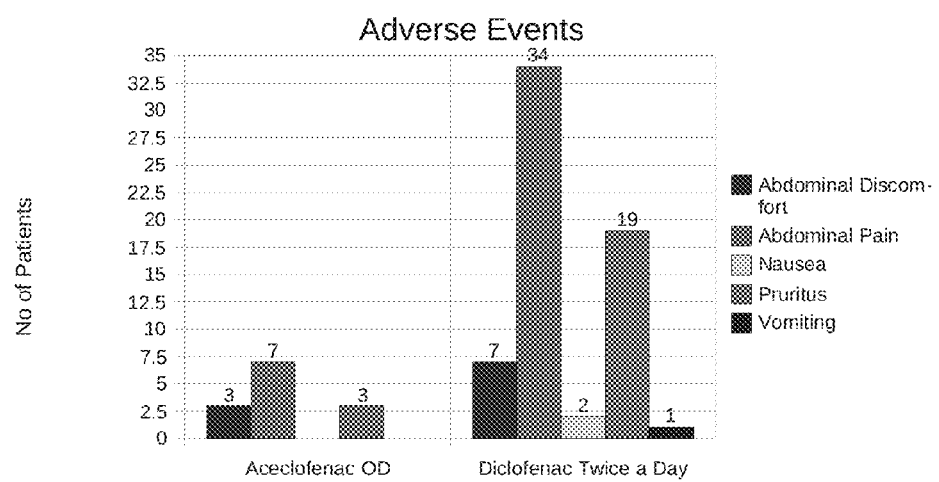
FIG. 10 illustrates a comparative reduction in Adverse drug reduction after Phase III clinical trials in 300 patients.

In yet another illustration of the embodiment of the invention, Example 5 is represented wherein an Evaluation of Efficacy and safety of Aceclofenac-SR (Aceclofenac OD-once daily formulation) injection in the treatment of Acute Lumbago is studied in A randomized Comparative Open Labeled Multicentric Trial. The present study was undertaken to evaluate the pain scores, analgesic effect of study drugs, with aceclofenac-SR (Aceclofenac OD) acting faster than diclofenac and is illustrated in FIG. 10. A total of 300 patients were randomly assigned to receive either aceclofenac-SR (150 patients) or Diclofenac (150 patients). The modified Schober's test (FIG. 8) showed progressive improvements at 8 hrs, 24 hrs and after 48 hrs of treatment in both groups, but the improvement was higher and significant (p<0.05) in the aceclofenac-SR (Aceclofenac OD) group than in the diclofenac at 8 hours, 24 hours and after 48 hours of treatment. Similarly at a 5% level of significance, aceclofenac-SR was found to be superior to diclofenac in terms of the other outcome measures including pain on movement, Functional impairment, pain on pressure in the lumbosacral region, muscle contraction in the lumbosacral region, Fewer adverse events (Most common AEs were abdominal pain, Pruritus) were reported in the aceclofenac-SR (Aceclofenac OD) group than the diclofenac group.

In yet another embodiment use of a controlled release parenteral formulation for preparation of an medicament is provided. The medicament may be used to relieve pain and inflammation in medical conditions include surgical pain, spasmodic pain, muscular pain, cramps, nociceptive pain, idopathic pain, neuropathic pain, psychogenic pain, phantom pain, accidental and sports injury pain, surgical pain and post surgical adhesion pain, rheumatoid arthritis, spondyloarthropathies particularly ankylating spondalosis, osteoarthritis, systemic lupus erythematosus and juvenile arthritis; asthma, bronchitis, preterm labor, tendonitis, bursitis, allergic neuritis, cytomegalovirus infection, apoptosis including HIV-induced apoptosis, lumbago, pain related to auto immune disorders.

Above disclosure describe a manner and method of making using the invention and sets forth the best mode contemplated by the inventor for carrying out his invention but is not to be construed as limiting. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications and equivalents of the described modes for carrying out the invention that are obvious to those skilled in formulation development or related fields are intended to be within the scope of the invention. The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

I claim:

1. A stable controlled release parenteral formulation for treatment of pain and inflammation, said formulation comprising an effective amount of:
   at least one active drug moiety,
      wherein said at least one active drug moiety is selected from the group consisting of aceclofenac, diclofenac, and a combination thereof;
   at least one solvent moiety,
      wherein said at least one solvent moiety is selected from the group consisting of triacetin, dimethyl isosorbide, and a combination thereof,
   wherein said formulation, upon administration, has a release profile comprising an immediate burst release;
   wherein said immediate burst release is followed by a sustained release of at least 18 to 24 hrs;
   wherein said immediate burst release and said sustained release of said drug moiety remains within a therapeutic window of said at least one active drug moiety;
   wherein said dimethyl isosorbide is present in a range of about 0.05 ml to about 0.7 ml:
   wherein said triacetin is present in a range of about 0.3 ml to about 3.0 ml; and
   wherein said at least one solvent and said at least one active drug moiety are present as a single unit injection.

2. The stable controlled release parenteral formulation as claimed in claim 1, wherein said at least one active drug moiety is present in a range of 1 mg to about 500 mg of said formulation.

3. The stable controlled release parenteral formulation as claimed in claim 1,
   wherein said at least one active drug moiety is aceclofenac or a pharmaceutically acceptable salts thereof;
   wherein said aceclofenac is present in a range of about 50 mg/ml to about 200 mg/ml of said formulation;
   wherein said at least one solvent moiety comprises dimethyl isosorbide and triacetin; and
   wherein a ratio of dimethyl isosorbide:triacetin is in a range of about 1:4.5 to about 1:5.5.

4. The stable controlled release parenteral formulation as claimed in claim 1,
   wherein said formulation is a liquid injection ready to use as said single unit injection,
   wherein a pH of said formulation is 5.0±1.0.

5. A method of effecting sustained release of a formulation as claimed in claim 1 for treatment of pain and inflammation along with reducing post surgical adhesions associated with medical conditions in an animal in need, said method comprising the steps of administering not more than one injection to a subject in need an effective amount of said formulation in a three days period.

6. The method of claim 5, wherein the pain and inflammation is selected from the group consisting of surgical pain, spasmodic pain, muscular pain, cramps, nociceptive pain, idiopathic pain, neuropathic pain, psychogenic pain, phantom pain, accidental and sports injury pain, surgical pain and post surgical adhesion pain, and wherein the medical conditions are selected from the group consisting of rheumatoid arthritis, spondyloarthropathies, ankylating spondalosis, osteoarthritis, systemic lupus erythematosus, juvenile arthritis, asthma, bronchitis, preterm labor, tendonitis, bursitis, allergic neuritis, cytomegalovirus infection, apoptosis including HIV-induced apoptosis, lumbago, and auto immune disorders.

7. The stable controlled release parenteral formulation as claimed in claim 1, configured such that the immediate burst release is initiated after less than 5 minutes of administration, followed by a sustained slow release over a period of time of at least 24 hours.

8. The stable controlled release parenteral formulation as claimed in claim 1, which is stable for a shelf life of 2 years.

9. The stable controlled release parenteral formulation as claimed in claim 1, characterized by an absence of polymer.

10. The stable controlled release parenteral formulation as claimed in claim 1, wherein the single unit injection of the controlled release parenteral formulation maintains its effect in a therapeutic window for 24 hrs or more.

* * * * *